United States Patent [19]

Leyendecker et al.

[11] Patent Number: 4,539,302
[45] Date of Patent: Sep. 3, 1985

[54] RECOVERY OF ZEROVALENT NICKEL COMPLEXES

[75] Inventors: William R. Leyendecker; Morris Rapoport, both of Orange, Tex.

[73] Assignee: E. I. Du Pont de Nemours and Company, Wilmington, Del.

[21] Appl. No.: 605,311

[22] Filed: Apr. 30, 1984

[51] Int. Cl.³ .................... B01J 31/40; C07C 120/02; C07C 121/26; C07F 15/04
[52] U.S. Cl. ............................... 502/24; 260/465.8 R; 502/162; 556/13
[58] Field of Search .................. 502/24, 26, 29, 162; 260/465.8 R, 439 R

[56] References Cited

U.S. PATENT DOCUMENTS

| | | | |
|---|---|---|---|
| 3,496,218 | 2/1970 | Drinkard | 260/465.8 |
| 3,631,191 | 12/1971 | Kane et al. | 502/162 |
| 3,766,237 | 10/1973 | Chia et al. | 260/465.3 |
| 3,773,809 | 11/1973 | Walter | 260/465.8 R |
| 3,818,068 | 6/1974 | Wells | 260/465.8 R |
| 3,903,120 | 9/1975 | Shook et al. | 260/439 R |
| 4,371,474 | 2/1983 | Rapoport | 260/465.8 R |
| 4,385,007 | 5/1983 | Shook | 260/465.8 R |
| 4,416,825 | 11/1983 | Ostermaier | 260/439 R |

Primary Examiner—P. E. Konopka

[57] ABSTRACT

Process for recovery of zerovalent nickel organophosphorus containing catalyst from a hydrocyanation product stream by controlling the level of unreacted mononitriles in the stream causing the thus treated stream to form two phases and recovering catalyst from the heavier phase.

9 Claims, No Drawings

RECOVERY OF ZEROVALENT NICKEL COMPLEXES

BACKGROUND OF THE INVENTION

1. Field of the Invention

The present process is directed to an improved utilization of zerovalent nickel complexes which are employed as catalysts for the production of dinitriles. More particularly, the present invention is directed to the recovery and recycle of nickel catalyst to thereby minimize loss of elemental nickel and optimize the production of a catalyst having a low ligand to nickel ratio.

2. Description of the Prior Art

U.S. Pat. No. 4,385,007 issued on May 24, 1983 discloses an improved process for the preparation of zerovalent nickel-organophosphorus ligand containing catalysts which are employed in the hydrocyanation reaction, which disclosure is incorporated herein by this reference.

U.S. Pat. No. 3,496,218 issued Feb. 17, 1970; U.S. Pat. No. 3,766,237 issued on Oct. 16, 1973; U.S. Pat. No. 3,903,120 issued on Sept. 2, 1975 and U.S. Pat. No. 3,773,809 issued on Nov. 20, 1973 disclose the general process conditions for catalyst preparation and product recovery to which the present invention can be applied.

U.S. Pat. No. 4,416,825 issued Nov. 22, 1983 discloses a continuous process for the preparation of zerovalent nickel complexes with organic phosphorus compounds, the product of which can be blended with the product of the present process.

The process of the present invention is especially effective in obtaining catalysts such as those used in the process described in U.S. Pat. No. 4,371,474 issued on Feb. 1, 1983, the disclosure of which is incorporated herein by this reference.

SUMMARY OF THE INVENTION

Process for recovery of a catalyst comprising zerovalent nickel and organophosphorus ligand from a dinitrile hydrocyanation product containing unreacted mononitriles wherein the recovered catalyst has a ligand to nickel ratio lower than the ligand to nickel ratio of the catalyst in the product fluid which process comprises controlling the level of unreacted mononitriles in the product fluid from the hydrocyanation to less than about 3–20%, preferably 5–15%, by weight based upon the weight of the product fluid and the ligand to nickel ratio less than about 9/1, preferably 5.0–7.8/1, causing the thus treated stream to form two phases usually by cooling to a temperature in the range 25°–65° C., separating the phases and returning at least a portion of the heavier phase to the hydrocyanation reaction. In one preferred embodiment a portion of the heavier phase is combined with catalyst prepared by reacting elemental nickel with organophosphorus ligand and catalyst subsequently recovered from the lighter phase and the combination introduced into the hydrocyanation reaction.

DETAILED DESCRIPTION OF THE INVENTION

The present invention can be employed to decrease elemental nickel usage and optimize catalyst preparation in any hydrocyanation process which employs zerovalent nickel catalyst to produce dinitriles. A particularly interesting hydrocyanation process involves the hydrocyanation of 3- and/or 4-pentenenitriles or mixtures thereof to produce adiponitrile. This dinitrile is an intermediate used in the production of hexamethylenediamine which in turn is used to produce polyhexamethyleneadipamide - a commercial polyamide useful in forming fibers, films and molded articles. Although 3- and/or 4-pentenenitriles are of particular interest, the hydrocyanation reaction can employ any nonconjugated ethylenically unsaturated organonitrile of from 4–20 carbon atoms, e.g., 2-methyl-3-butenenitrile.

The catalysts to which the process of the present invention is applied are those represented by the formula $NiL_4$ where L is a ligand represented by the formula $P(OAr)_3$ where Ar is the same or different and is an aryl group having up to 18 carbon atoms, e.g., methoxyphenyl, toly, xylyl and phenyl. Meta- and para-tolyl and mixtures thereof are preferred aryl groups. The amount of ligand which is greater than the four ligands forming the zerovalent nickel complex as described by the foregoing formula is termed "excess ligand". More particularly, those catalysts having a minimum ligand to nickel ratio are especially amenable to production according to the present process. Catalysts such as those described in U.S. Pat. No. 4,371,474 discussed hereinabove are of particular interest.

Generally, the catalysts are employed with promoters such as zinc chloride or aryl boranes of the formula $BR_3$ wherein R is the same or different and is an aryl or substituted aryl group having 6–12 carbon atoms, e.g., phenyl, orthotoly, paratolyl, biphenyl, chlorophenyl and bromophenyl. Triphenylborane is the preferred promoter. The process of the present invention is conducted before the hydrocyanation product fluid is subjected to extraction as disclosed in U.S. Pat. No. 3,773,809.

A typical product fluid obtained from the hydrocyanation of 3-pentenenitrile (3-PN) and/or 4-pentenenitrile (4-PN) to produce adiponitrile (ADN) using a zerovalent nickel catalyst of the formula $NiL_4$ wherein L is a neutral ligand of tri-(meta and para)tolylphosphite (TTP) and a promoter has the composition set forth in Table I.

TABLE I

| Compound | Amount (% by Weight) |
|---|---|
| $NiL_4$ | 10–20 |
|  | (0.4–0.8 as Ni) |
| Excess L | 2.4–24 |
| 3- and 4-PN | 15–40 |
| ADN + DN* | 72–15 |
| Promoter | 1.0–0.05 |

*Dinitriles other than ADN, e.g., 2-methyl-glutaronitrile and ethylsuccinonitrile.

The catalyst contained in the heavier phase obtained using the process of the present invention has a lower total ligand to nickel ratio relative to that ratio in the product fluid because excess ligand is not completely removed. This is quite advantageous because it provides a catalyst having a very low ligand to nickel ratio which is expensive to prepare directly from elemental nickel.

If the concentration of 3- and/or 4-PN in the product fluid is maintained or reduced to within the range of 3–20%, preferably 5–15%, it has been found that the product fluid can be made to form two phases with the more dense (heavier) phase containing substantially more catalyst of differing composition than the less dense phase. Levels greater than about 30% render the present process impractical. Control within the abovementioned ranges can be achieved by adjustment of reaction conditions, i.e., to effect conversion, etc., or by removing a portion of the mononitriles from the hydrocyanation product fluid, e.g., by flashing or distillation.

It has also been determined that the ability to form two phases of the desired composition from the hydrocyanation product fluid depends upon variables in addition to PN concentration. The relative amounts of other components of the product fluid are important to obtaining a satisfactory separation of phases. The molar ratio of total organophosphorus ligand (L4 plus Excess L) to zerovalent nickel introduced into the reaction must be maintained at less than about 9/1 and preferably in the range 5.0–7.8/1. This ratio is controlled by adjusting the ligand to nickel ratio in the catalyst introduced into the hydrocyanation taking into account the amount of nickel which is oxidized (deactivated) in the reaction, i.e., the deactivation of the nickel causes an increase in the ratio of ligand to zerovalent nickel. Thus, if the catalyst is introduced into the hydrocyanation reaction at a ligand to zerovalent nickel ratio close to 9/1 it is quite possible that the ratio in the product fluid will exceed this maximum ratio thereby frustrating phase formation.

The molar ratio of dinitriles (DN) including adiponitrile (ADN), i.e., (ADN+DN) to zerovalent nickel, is also an important variable. In order to assure the formation of a significant amount of concentrated catalyst phase, this ratio must be maintained in the range 10–75 and preferably 20–40 by controlling the ratio of HCN to nickel introduced into the reaction.

One skilled in the art should appreciate that if the product stream contains a high level of ligand, in order to maximize the catalyst recovery, it is advantageous to remove more unreacted pentenenitriles and to conduct the process at the lower end of the stated range, i.e., closer to 3%. Operation at this end of the range is advantageous when the organophosphorus ligand to nickel ratio approaches 9/1.

The product stream is usually maintained at a temperature in the range 25°–100° C. and preferably 35°–65° C. during phase formation to obtain optimum catalyst recovery.

The following examples are presented to illustrate but not to restrict the present invention. Parts and percentages are by weight unless otherwise specified.

EXAMPLE 1

In the following examples the starting material was a product fluid from the hydrocyanation of 3- and 4-pentenenitriles using tetrakis(tri-m and p-tolylphosphite) nickel zero catalyst using triphenylborane as a promoter. The stream had the approximate analysis set forth in Table II.

TABLE II

| Compounds | Amount (% by Weight) |
|---|---|
| NiL4 | 18 |
| 3- and 4-PN | 33 |
| ADN + DN | 33 |
| Excess L | 10 |

TABLE II-continued

| Compounds | Amount (% by Weight) |
|---|---|
| TTP/Ni | 6.3/1 |
| ADN + DN/Ni | 25/1 |

This material was directed to a single stage continuous vacuum flasher which consisted of a recirculation loop containing a vaporizer, a vapor liquid separator and a circulation pump. Material was introduced into the circulation loop and the level in the separator was maintained by withdrawing material from the pump discharge. Vapors from the separator were condensed and recovered. The flasher was operated at a temperature of 145° C. and 50 mm Hg pressure. Approximately 100 parts of the liquid product from the flasher was collected and introduced into a tube maintained at approximately 50° C. wherein two phases were formed. Each phase was then removed, weighed and analyzed. The results are set forth in Table III. It should be noted that 90% of the NiL4 is in the lower phase while approximately 90% of the dinitriles are in the upper phase. This lower phase is suitable for direct recycle to the hydrocyanation process and/or combination with freshly prepared or other recycle catalyst.

EXAMPLE 2

Approximately 25 parts of a mixture having a composition set forth in Table III was prepared and agitated and heated in the absence of air to a temperature of approximately 123° C. whereupon the mixture became a single liquid phase. This material was permitted to cool to approximately 50° C. during which time two phases separated. Each phase was recovered, weighed and analyzed. The results are set forth in Table III. Approximately 85% of the NiL4 was collected in the lower phase whereas 90% of the dinitriles were collected in the upper phase.

EXAMPLE 3

A product fluid from the hydrocyanation of 3- and 4-pentenenitriles having the composition set forth in Table III was directed to a flash evaporator operated at a temperature of approximately 112° C. and a pressure of 60 mm Hg to produce a stream of the composition and quantity shown in Table III. The stream was cooled to 55° C. and the cooled stream was then continuously directed to a decanter where the two phases were continuously separated. Each portion of 136 parts were removed and analyzed periodically. The results were averaged over a four-day period and reported in Table III.

The lower phase is mixed with catalyst prepared according to U.S. Pat. No. 3,903,120 thereby obtaining a catalyst having a low TTP/Ni ratio. The upper phase is extracted with cyclohexane according to U.S. Pat. No. 3,773,809 and the remaining catalyst is recovered. The cyclohexane is stripped from the extract, yielding a catalyst having a high TTP/Ni ratio. The catalysts having the high and low TTP/Ni ratios are blended and used as catalysts for the hydrocyanation of 3- and/or 4-PN in disclosed in U.S. Pat. No. 4,371,474.

TABLE III

| Components (weight %) | Example 1 | | | Example 2 | | | Example 3 | | | |
|---|---|---|---|---|---|---|---|---|---|---|
| | Product Fluid | More Dense Phase | Less Dense Phase | Product Fluid | More Dense Phase | Less Dense Phase | Product Fluid Before Vaporization | Product Fluid After Vaporization | More Dense Phase | Less Dense Phase |
| Unreacted Mononitrile (PN) | 3 | 2 | 4 | 8 | 4 | 9 | 41 | 12 | 6 | 12 |
| Dinitrile (ADN + DN) | 43 | 12 | 63 | 43 | 10 | 57 | 36 | 54 | 13 | 65 |
| $NiL_4$ | 28 | 64 | 5 | 28 | 72 | 10 | 15 | 22 | 59 | 11 |
| Excess L | 16 | 16 | 17 | 15 | 5 | 19 | 8 | 12 | 17 | 9 |
| Parts | | | | | | | | | | |
| Unreacted Mononitrile (PN) | 3 | 0.8 | 2 | 2 | 0.3 | 2 | 55 | 16 | 2 | 12 |
| Dinitrile (ADN + DN) | 40 | 4 | 36 | 11 | 0.8 | 10 | 49 | 73 | 4 | 66 |
| $NiL_4$ | 27 | 24 | 3 | 7 | 6 | 2 | 21 | 31 | 20 | 11 |
| Excess L | 16 | 6 | 10 | 4 | 0.4 | 3 | 11 | 16 | 6 | 9 |
| TTP/Ni | 6 | 5 | 18 | 6 | 4 | 12 | 6 | 6 | 5 | 7 |
| DN/Ni | 21 | 3 | 170 | 21 | 2 | 77 | 33 | 33 | 3 | 80 |

We claim:

1. A process for recovery of a catalyst comprising zerovalent nickel and organophosphorus ligand from a dinitrile hydrocyanation product fluid containing unreacted mononitriles wherein the recovered catalyst has a ligand to nickel ratio lower than the ligand to nickel ratio of the catalyst in the product fluid which process comprises controlling the level of unreacted mononitriles in the product fluid from the hydrocyanation to about 3–20% by weight based upon the weight of the product fluid and the ligand to nickel molar ratio less than about 9/1, causing the thus treated stream to form two phases, separating the phases and returning at least a portion of the heavier phase to the hydrocyanation reaction.

2. The process of claim 1 wherein the product fluid is maintained at a temperature in the range 25°–65° C.

3. The process of claim 1 wherein unreacted nitrile is removed from the product fluid to obtain a concentration thereof in the range 5–15%.

4. The process of claim 2 wherein unreacted nitrile is removed from the product fluid to obtain a concentration thereof in the range 5–15%.

5. The process of claim 1 wherein at least a portion of the heavier phase is combined with catalyst prepared by reacting elemental nickel with organophosphorus ligand and the combination introduced into the hydrocyanation reaction.

6. The process of claim 4 wherein at least a portion of the heavier phase is combined with catalyst prepared by reacting elemental nickel with organophosphorus ligand and catalyst subsequently recovered from the lighter phase and the combination introduced into the hydrocyanation reaction.

7. The process of claim 1 wherein molar ratio of dinitrile hydrocyanation reaction product to zerovalent nickel in the product fluid is maintained in the range 10–75.

8. The process of claim 4 wherein the ligand to nickel molar ratio is maintained in the range 5.0–7.8/1.

9. The process of claim 8 wherein at least a portion of the heavier phase is combined with catalyst prepared by reacting elemental nickel with organophosphorus ligand and catalyst subsequently recovered from the lighter phase and the combination introduced into the hydrocyanation reaction.

* * * * *